United States Patent
Nagy

(10) Patent No.: US 6,989,676 B2
(45) Date of Patent: *Jan. 24, 2006

(54) APPARATUS AND METHOD FOR SENSING PARTICLE AND WATER CONCENTRATIONS IN A MEDIUM

(75) Inventor: Louis L. Nagy, Warren, MI (US)

(73) Assignee: Delphi Technologies, Inc., Troy, MI (US)

( * ) Notice: Subject to any disclaimer, the term of this patent is extended or adjusted under 35 U.S.C. 154(b) by 71 days.

This patent is subject to a terminal disclaimer.

(21) Appl. No.: 10/688,647

(22) Filed: Oct. 17, 2003

(65) Prior Publication Data

US 2004/0135585 A1 Jul. 15, 2004

Related U.S. Application Data

(63) Continuation-in-part of application No. 10/341,567, filed on Jan. 13, 2003, now Pat. No. 6,788,072, and a continuation-in-part of application No. 10/649,531, filed on Aug. 27, 2003, now Pat. No. 6,891,383.

(51) Int. Cl.
*G01R 27/32* (2006.01)
*G01R 27/08* (2006.01)

(52) U.S. Cl. ............... 324/643; 324/645; 324/698
(58) Field of Classification Search ........... 324/698, 324/639, 640, 664, 645, 553
See application file for complete search history.

(56) References Cited

U.S. PATENT DOCUMENTS

| 4,042,879 A | 8/1977 | Ho et al. ............. 324/636 |
| 4,345,202 A | 8/1982 | Nagy et al. .......... 324/642 |
| 4,477,771 A | 10/1984 | Nagy et al. .......... 324/636 |
| 4,503,384 A | 3/1985 | Nagy et al. .......... 324/690 |
| 4,543,823 A | 10/1985 | Nagy et al. ......... 73/304 C |
| 4,544,880 A | 10/1985 | Nagy et al. .......... 324/642 |
| 5,103,181 A * | 4/1992 | Gaisford et al. ...... 324/637 |
| 5,157,340 A | 10/1992 | Walton et al. ........ 324/641 |
| 5,754,055 A * | 5/1998 | McAdoo et al. ...... 324/636 |
| 5,898,308 A | 4/1999 | Champion ........... 324/643 |
| 6,459,995 B1 * | 10/2002 | Collister ................ 702/23 |
| 6,519,034 B1 | 2/2003 | Engler et al. ......... 324/639 |
| 6,788,072 B2 * | 9/2004 | Nagy et al. .......... 324/639 |
| 2004/0239344 A1 * | 12/2004 | Hu ....................... 324/698 |

* cited by examiner

*Primary Examiner*—Anjan Deb
(74) *Attorney, Agent, or Firm*—Jimmy L. Funke

(57) ABSTRACT

A method and apparatus for detecting soot and/or water concentrations in diesel engine oil having a dielectric constant may include a device for measuring a change in the dielectric constant at a first frequency, a device for measuring a change in the dielectric constant at a second frequency and a processor configured to calculate at least one of a percentage of soot content and a percentage of water content as a function of the measured changes in the dielectric constant at the first and second frequencies. The first frequency may be within approximately the ultrasonic and sub-AM frequency bands and the second frequency may be within approximately the microwave frequency band.

13 Claims, 4 Drawing Sheets

APPARATUS AND METHOD FOR SENSING PARTICLE AND WATER CONCENTRATIONS IN A MEDIUM

REFERENCE TO RELATED APPLICATIONS

This application is a Continuation-In-Part of U.S. application Ser. No. 10/341,567 filed Jan. 13, 2003, now U.S. Pat. No. 6,788,072 and a Continuation-In-Part of U.S. application Ser. No. 10/649,531 filed Aug. 27, 2003, now U.S. Pat. No. 6,891,383.

BACKGROUND OF THE INVENTION

This invention relates in general to sensors and in particular to an apparatus and method for sensing the accumulation of soot and/or water in diesel engine oil.

During usage of a diesel engine, for example, the crankcase oil gradually experiences particle accumulation in the form of soot, which is a combustion by-product, in the combustion chamber of the engine. Portions of soot may then be transferred in small amounts to the crankcase oil. When the soot builds up to an unacceptable amount, such as a predetermined threshold percentage, the lubricating quality of the oil is diminished. When this occurs it may be necessary to change the crankcase oil whenever the soot content reaches an unacceptable value. For this purpose, it is desirable to measure the soot content percentage in the crankcase oil in order to detect the presence of the unacceptable percentage of soot.

Further, diesel engine oil is degraded by the presence of soot particles that increasingly accumulate with engine use. In addition, diesel oil is degraded as its additives are depleted and oil acidity is increased. It is becoming increasingly important for the efficient maintenance of diesel engines to have an on-board sensor that will accurately detect soot concentrations.

Microwave probes are known to be used for detecting soot in diesel engine oil such as the one disclosed in U.S. Pat. No. 4,345,202 issued to Nagy et al. Nagy discloses a microwave probe used to detect soot up to concentration levels of about five percent. This sensor used a single microwave frequency to characterize the real part of the relative permittivity for used diesel oil. From this data it was determined that the microwave probe could be used to measure the soot content of up to about five percent. However, more advanced diesel engines in today's markets may require detecting soot concentrations at levels greater than five percent. This new requirement for detecting higher soot concentrations presents problems for existing electromagnetic sensors, which have not been able to accurately measure the soot content in diesel engine oils when soot content is greater than about four percent. Above a four percent soot concentration level, various small soot particles appear to agglomerate to form large electrically lossy particles. These agglomerate particles adversely affect the ability of these sensors to accurately measure soot concentrations because of the change in the particles geometry and increase in electrical losses.

It is known that even though soot particles are conductors rather than dielectric they can increase the relative permittivity or relative dielectric constant of a dielectric fluid, such as diesel oil. This is because very small conductive particles in a dielectric form what is commonly called an artificial dielectric. Thus, the proposition that the soot content of engine oil can be measured by measuring the relative permittivity of the oil is viable provided there are no other factors affecting the oil's relative permittivity. The buildup of non-soot contaminants during engine service, oil formulations and oil additives may influence the oil's relative permittivity. If these variables significantly influence relative permittivity then that relative permittivity parameter cannot be used as a measurement of soot content. That is, non-soot constituents of engine oil can contribute enough to relative permittivity measurements to make those measurements unsuitable for a measure of soot content.

BRIEF DESCRIPTION OF THE INVENTION

An apparatus and method is provided for detecting soot and water concentrations in diesel engine oil. Soot concentrations may be measured up to about eight percent and water concentrations up to about ten percent. Detecting soot concentrations may prevent oil from being changed prematurely, which may provide a significant economic gain to an operator of a fleet of vehicles. Detecting water concentrations may be useful to determine whether any water gasket leaks are present in the engine of a vehicle, for example.

A method and apparatus for detecting soot and/or water concentrations in diesel engine oil having a dielectric constant is provided that may include a device for measuring a change in the dielectric constant at a first frequency, a device for measuring a change in the dielectric constant at a second frequency and a processor configured to calculate at least one of a percentage of soot content and a percentage of water content as a function of the measured changes in the dielectric constant at the first and second frequencies. The first frequency may be within approximately the ultrasonic and sub-AM frequency bands and the second frequency may be within approximately the microwave frequency band.

DETAILED DESCRIPTION OF THE INVENTION

Figure 1:
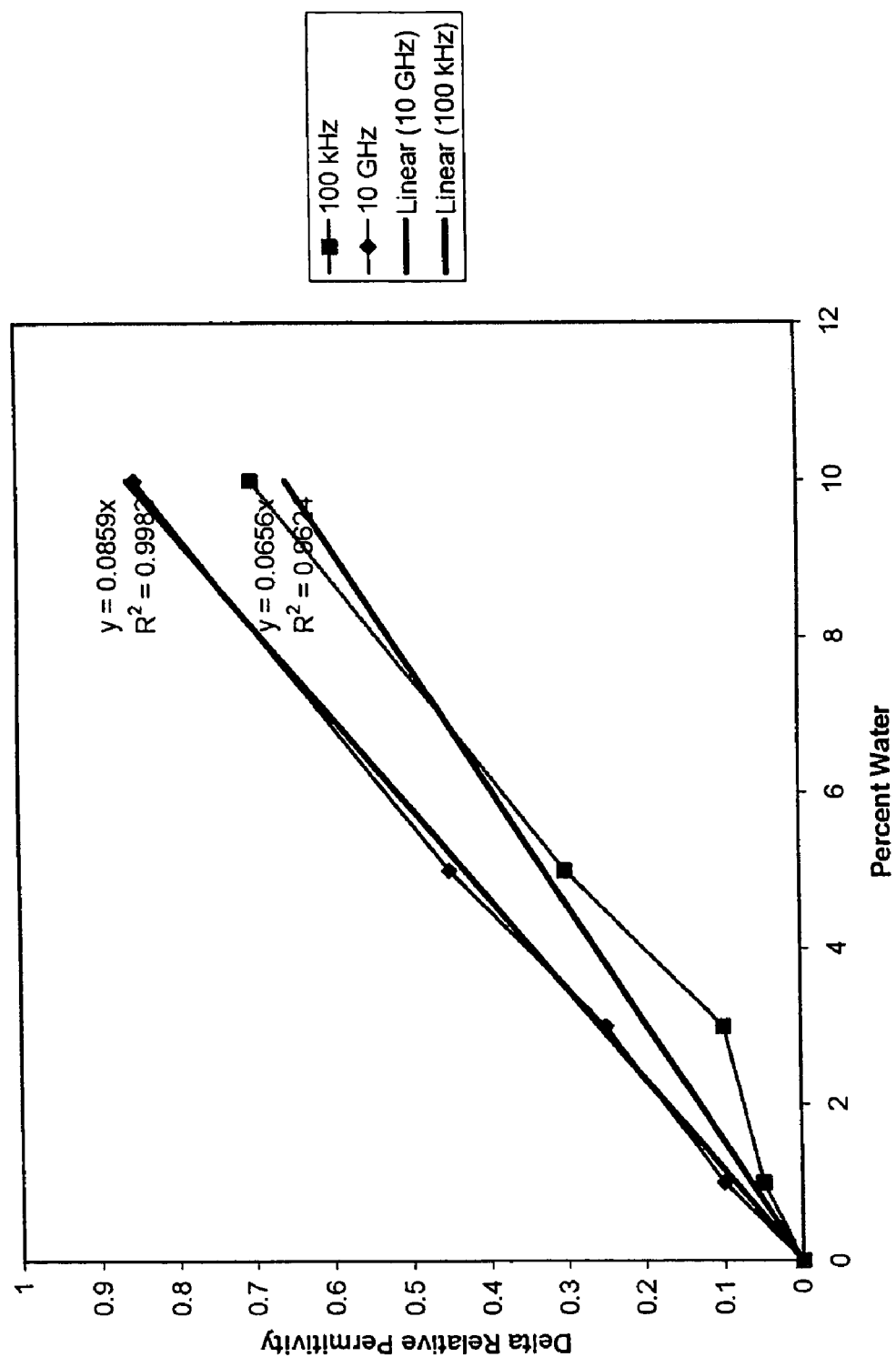
FIG. 1 is a graph plotting the percent of water in oil against a change in the oil's relative permittivity.

It has been determined that the soot content of diesel oil is proportional to the oil's $\epsilon/\epsilon''$ value at microwave frequencies where $\epsilon$ represents the oil's total dielectric constant (i.e., $\epsilon=\epsilon'-j\epsilon''$ where $\epsilon'$ is the real part and $\epsilon''$ is the loss part of $\epsilon$) and $\epsilon''$ represents the loss portion of the oil's total dielectric constant. For oils containing a low concentration of soot and hence low electrical loss (i.e., $\epsilon''$ can be neglected), the measurement of the oil's dielectric total constant ($\epsilon$) will provide a good approximation of $\epsilon'$ (i.e., $\epsilon \approx \epsilon'$) that will then provide accurate information about soot content. When significant electrical loss exists in an oil (because of high soot concentrations), this loss will bias the measurement of $\epsilon$ and $\epsilon''$ must be taken into account for determining $\epsilon'$. One aspect allows for dividing the loss component out of the calculations for determining changes in the oil's dielectric constant for accurately determining the percentage of soot content in the oil up to and above four percent.

One aspect allows for detection of both soot and water concentrations in a medium such as diesel oil. At microwave frequencies, the effects of water concentrations on the oil's normalized (real part) dielectric characteristics are similar to the effects of soot, for the same concentrations. However, at low concentrations of water in oil, such as not exceeding one percent, water will have only a minor effect on the determination of soot concentrations. One embodiment allows for using microwave frequencies for measuring or estimating soot concentrations and sub-AM band frequencies for measuring or estimating water concentrations. It will be recognized by those skilled in the art that various embodiments of the invention may be used for detecting particle and water concentrations in various mediums other than diesel oil.

Various exemplary embodiments of the invention may be implemented using appropriately configured sensors such as embodiments of the sensors and sensor systems disclosed in U.S. Pat. Nos. 4,345,202, 4,477,771, 4,503,384, 4,543,823 and 4,544,880 all issued to Nagy et al., for example, all of which are specifically incorporated herein by reference in their entirety.

One aspect of the invention allows for establishing a first detector voltage level that is generated by a first frequency to produce a first waveform, such as a first voltage standing wave (VSW), within at least a portion of diesel oil, or other medium under investigation, for use in measuring soot concentrations. This first frequency may be in the microwave range of frequencies of between about 8 GHz and 12 GHz and in an exemplary embodiment is approximately 10 GHz. The voltage standing wave may have a voltage null point or condition placed at a known sampling or detection point. The sampling or detection point may be a point on a soot sensor, such as an embodiment described below, for detecting voltage levels, such as with a conventional RF detector. The first detector voltage level may be a baseline voltage level and may be established in clean or fresh oil that has a zero or near zero soot content. For example, an embodiment allows for the baseline voltage level to be established in oil within the sump of a vehicle immediately or shortly after the oil has been changed. Other embodiments allow for the baseline to be established in oil prior to the oil being placed within the sump of a vehicle. Alternate embodiments allow for the baseline voltage to be established in a medium having measurable soot content that is greater than zero, for example, to measure further changes to that soot content.

Another aspect of the invention allows for measuring a first capacitance level within at least a portion of diesel oil, or other medium under investigation, for use in measuring water concentrations. The first capacitance may be measured at a frequency in the ultrasonic and sub-AM frequency band of between about 20 khz and 1 MHz and in an exemplary embodiment is approximately 100 khz. The first capacitance level may be a baseline capacitance level and may be established in clean or fresh oil that has a zero or near zero water content. For example, an embodiment allows for the baseline capacitance level to be established in oil within the sump of a vehicle immediately or shortly after the oil has been changed. Other embodiments allow for the baseline to be established in oil prior to the oil being placed within the sump of a vehicle. Alternate embodiments allow for the baseline capacitance level to be established in a medium having measurable water content that is greater than zero, for example, to measure further changes to that water content.

Once establishing the baseline first voltage and capacitance levels described above, it may be desirable to subsequently measure the soot and/or water content in the oil. With respect to soot content, this may be accomplished by using a voltage controlled frequency oscillator to generate a second signal frequency signal within the first frequency microwave band that produces a second standing waveform, within at least a portion of the oil under investigation for soot content. A voltage null point or condition of the standing waveform for the second frequency may not be located at the respective detection point of the standing waveform for the first frequency due to changes to the oil's dielectric properties. This second waveform null point may be moved to the first waveform detecting point by changing the tuning voltage and therefore the frequency of the variable frequency oscillator. An exemplary embodiment allows for placing the voltage null point associated with the second standing wave at the first waveform detection point after a vehicle's engine has run for a period of time. The difference between the first voltage and the second tuning voltage of the oscillator may be used to measure a change in the relative dielectric constant or relative permittivity of the oil at microwave frequencies. With respect to water content, a change in the oil's relative dielectric constant may be determined by taking the difference between the baseline capacitance level and the capacitance level of the oil under investigation.

One aspect of the invention allows for measuring or estimating the soot and/or water content of diesel oil in terms of the change in the relative dielectric constant of the oil measured at multiple frequencies. An embodiment of the invention measures this change at a first frequency and a second frequency band. The first frequency band may be within approximately the microwave band of frequencies and the second frequency band within approximately the sub-AM band of frequencies. It has been determined that measuring the change in the relative dielectric constant within these two frequency ranges allows for measuring the soot and/or water content of the oil by using a system of linear equations described below. It will be appreciated that other combinations of ranges may be used provided the frequencies are far enough apart so that undesirable affects from oil additives or emulsifiers, for example, do not adversely influence measuring changes in the oil's relative dielectric constant. For example, an embodiment allows for the first frequency range to be about 1 GHz to 20 Ghz and the second frequency range to be about 20 kHz to 1 MHz.

Figure 2:
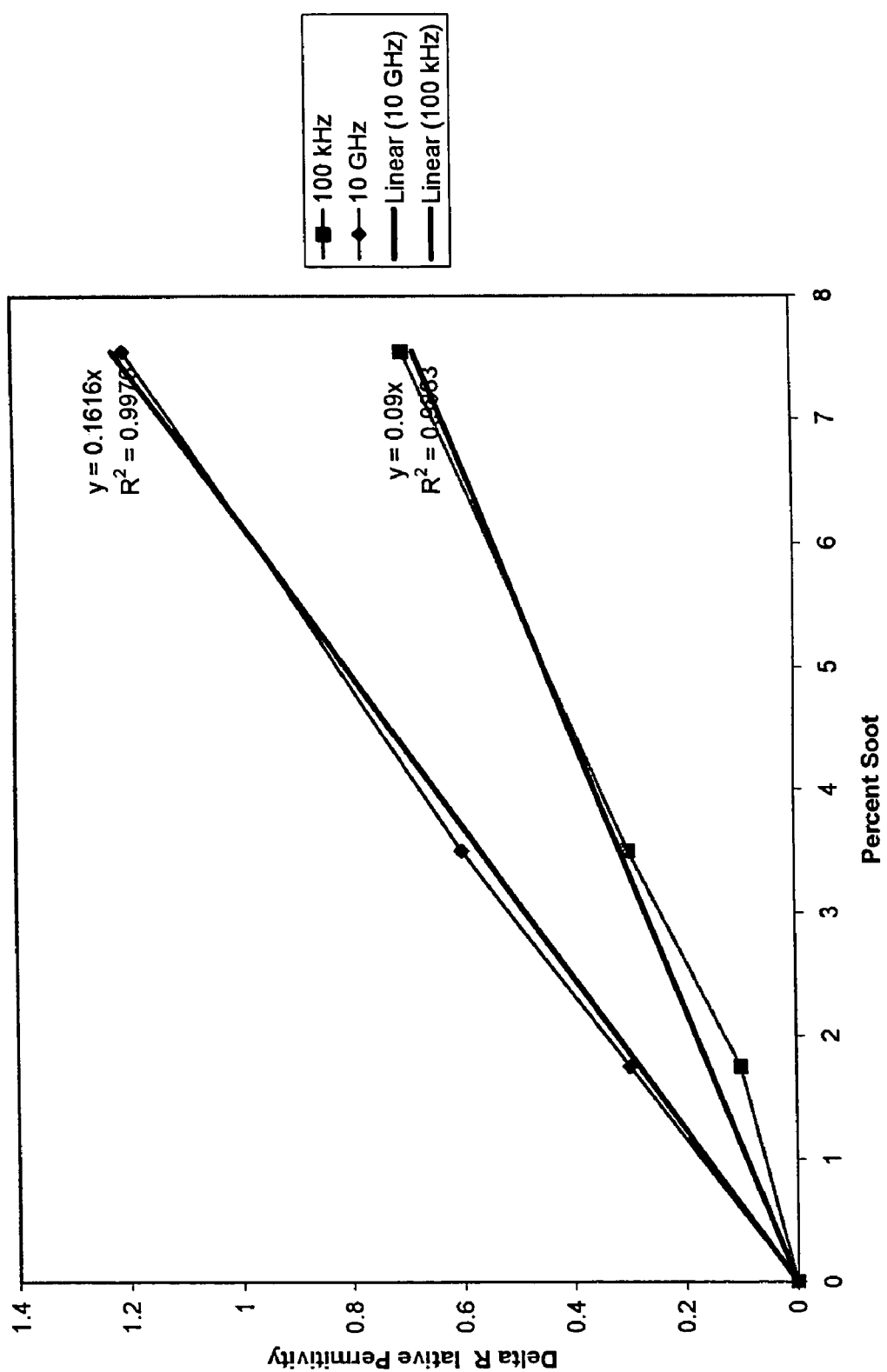
FIG. 2 is a graph plotting the percent of soot in oil against a change in the oil's relative permittivity.

The graphs of FIGS. 1 and 2, illustrate empirical data obtained through measurements conducted on diesel oil at approximately 100 KHz and approximately 10 GHz. FIG. 1 plots the change in the relative dielectric constant or permittivity ("Delta Relative Permittivity") against the percent of water found in the oil under investigation. FIG. 2 plots the Delta Relative Permittivity against the percent of soot found in the oil. The Delta Relative Permittivity may be measured as described above or it may be measured using known techniques. The equation representative of each plotted curve and their respective correlation coefficient are also illustrated.

One aspect allows for summing the effect of water and soot on the oil at these frequencies to arrive at the following equations:

$$Y = 9S + 6.6W \qquad (1);$$

and $$X = 16.2S + 8.6W \quad (2)$$

where:
Y=the Delta Relative Permittivity of the oil measured at approximately 100 kHz
X=the Delta Relative Permittivity of the oil measured at approximately 10 GHz.
S=the percentage soot content in the oil; and
X=the percentage water content in the oil.

Rearranging the above equations results in:

$$S = 0.22X - 0.29Y \quad (3);$$

and $$W = 0.54Y - 0.30X \quad (4)$$

Equations (3) and (4) allow for determining the concentration of soot ("S") and the concentration of water ("W") from measured changes in the relative dielectric constant referenced to fresh or clean oil. It has been determined that equations (3) and (4) may be used for soot concentrations up to about four to five percent. For soot concentrations higher than this, it may be necessary to take into account the loss effect of the dielectric constant depending on the accuracy desired. In this respect, the "X" term in equations (3) and (4) may include the loss effect of the change in the dielectric constant measured at microwave frequencies. In an exemplary embodiment, the change in the relative dielectric constant of oil under investigation may be measured or estimated at microwave frequencies by the equation (5), which accounts for the loss effect:

$$\frac{\text{oscillator tuning voltage for "clean oil"} - \text{oscillator tuning voltage for "dirty oil"}}{\text{null voltage level of "dirty oil"}} \quad (5)$$

For example, the voltage level of "clean oil" may be the baseline voltage level associated with the first standing wave, and the voltage level and the null voltage level of "dirty oil" may be the respective voltage levels associated with the second standing wave generated in the oil under investigation.

Figure 3:
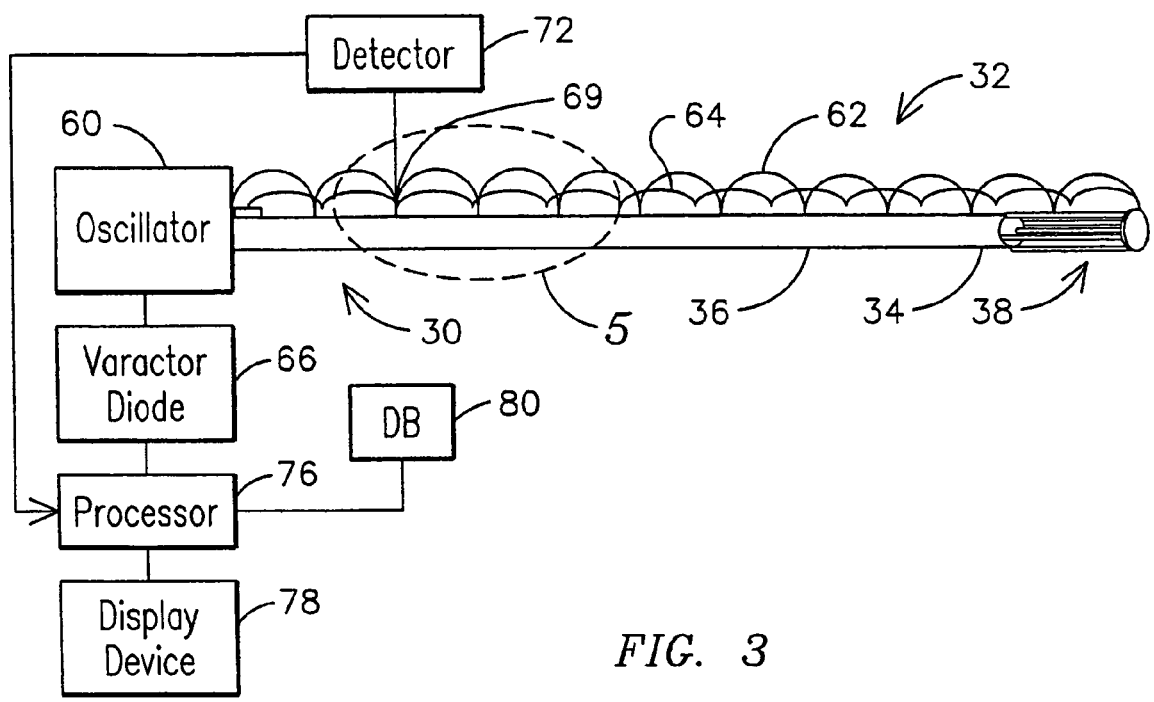
FIG. 3 is a schematic of an exemplary embodiment of a probe for measuring a change in the relative permittivity of oil at microwave frequencies.

An embodiment of the invention allows for using a first probe for measuring the increase in oil's relative permittivity within the microwave frequency range and a second probe for measuring the increase in oil's relative permittivity within the ultrasonic and sub-AM frequency bands. FIG. 3 illustrates an exemplary embodiment of a first probe 30 that may be used to measure or detect the increase in oil's relative permittivity in the microwave frequency range. Probe 30 may include a coaxial circuit such as an elongated conductor portion 32 configured to be inserted within a sump of an internal combustion engine, for example, so that the distal end 34 may be immersed in oil that is contained within the sump. The portion 32 may be fabricated from a standard coaxial cable 36 having a probe portion 38 affixed to the distal end 34. Probe portion 38 may be constructed in a substantially similar manner and be made of substantially the same materials as disclosed and described in U.S. Pat. No. 4,503,384 issued to Nagy et al., for example.

Figure 4:
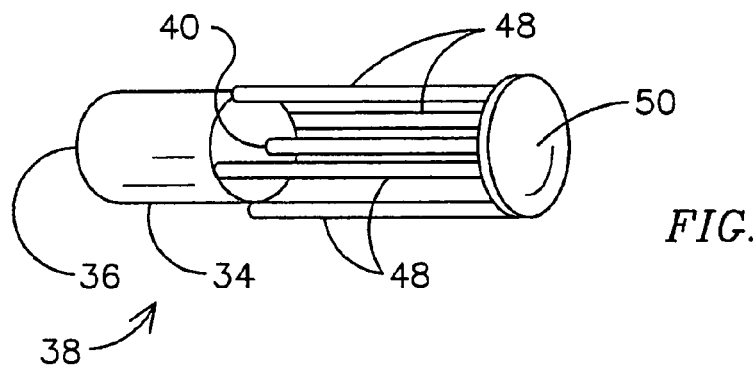
FIG. 4 is an enlarged view of the probe of FIG. 3.

As shown best in FIG. 4, the probe portion 38 forms a resonate structure and may include a set of substantially parallel wires. In an exemplary embodiment the resonate structure may include a center wire 40, which may be the center wire of the coaxial cable 36, and four exterior wires 48. The exterior wires 48 may be joined at one end to the outer sheath of the coaxial cable 36 in a conventional manner, such as welding, soldering, etc. and at the other end to a conductive shorting plate 50 in a similar manner. The center wire 40 may also be connected to the shorting plate 50 in a conventional manner such as by welding. Thus, the probe portion 38 forms a cage-like structure characterized by a plurality of spaced wires 40, 48 shorted at one end in an open configuration to allow oil or another medium to flow freely there between without pockets or other obstacles to trap or otherwise impede the free flow of the medium.

Figure 5:
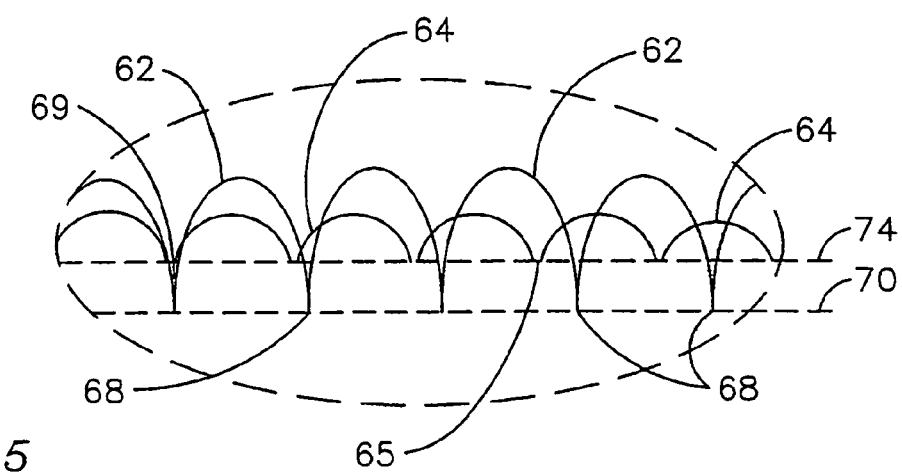
FIG. 5 is an enlarged view of a portion of the probe of FIG. 3.

FIG. 3 also illustrates an oscillator 60 that may be used to generate the first voltage standing waveform 62 and the second voltage standing waveform 64. The first waveform 62 and second waveform 64 may be first and second standing waves and may be formed by the respective forward waves from the oscillator 60 and the respective waves reflected from the resonating cavity structure formed by the probe portion 38. Oscillator 60 may be a conventional oscillator and in one exemplary embodiment may be a varactor-tuned oscillator that may produce variable frequencies in the microwave range, for example, between about 8 GHz and 12 GHz ("X-band"). It will be recognized by those skilled in the art that other frequencies may be used as a function of the medium under inspection, its dielectric properties and/or the electrical loss properties of the particles in the medium. A varactor diode 66 may be used to selectively vary the frequencies generated by the oscillator 60. As described above, first waveform 62 may be a standing wave generated at a first frequency by the oscillator 60 at a first voltage level where the first waveform 62 has a voltage null point or condition 68, as best shown in FIG. 5. Voltage null point 68 may be established at a fixed detection or sampling point 69 and has an associated first null voltage level 70.

As suggested above, the first voltage null level may be used to establish a baseline voltage level for clean or fresh oil having zero soot content. Subsequent voltage levels associated with changes in the oil's relative dielectric constant may be referenced to this voltage level for measuring soot content in the oil. The elongated conductor portion 32 may be inserted into an engine's sump so that the probe portion 38 is immersed in the oil. As the soot content changes in the oil over time, the null point 68 may shift longitudinally along the coaxial cable 36 in response to changes in the dielectric properties of the oil.

One aspect of the invention allows for oscillator 60 to produce the second voltage standing waveform 64 for use in measuring the change in the oil's relative dielectric constant. Oscillator 60 may be controlled so that the null point 65 of the second waveform 64 is moved back to or placed at the fixed detection or sampling point 69. A second frequency and corresponding second voltage level causing that frequency may be determined with respect to null point 65 positioned at detection point 69, using known techniques. A detector 72, which may be a known microwave or diode detector in one exemplary embodiment, may be used to detect a signal associated with this second null voltage level 74 for the oil undergoing soot content investigation. Detector 72 may also detect the first null voltage level 70. Data indicative of the signal levels associated with the first and second null voltage levels 70, 74 may be transmitted from the detector 72 to a microcontroller such as processor 76. Processor 76 may be configured to calculate the change in the relative dielectric constant of the oil within the microwave range of frequencies by taking the difference between the first voltage and the second voltage that generated the first and second waveforms, respectively. A database 80 may be provided that allows for storing data associated with exemplary embodiments of the present invention. This data may be retrieved and processed by processor 76, which may be configured to calculate and output data indicative of the percentage soot and/or water content of oil to a display device 78. An exemplary embodiment of device 78 may be a conventional indicator on the dashboard of a vehicle, for example.

Figure 6:
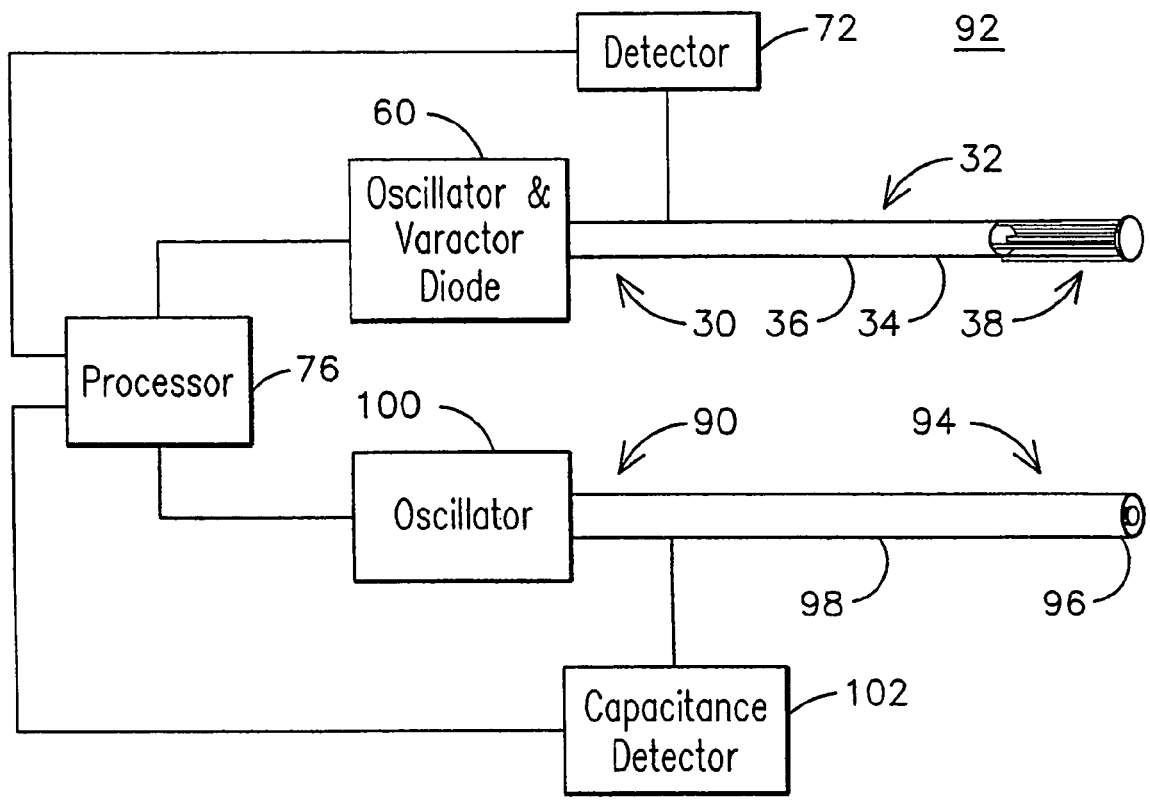
FIG. 6 is a schematic of an exemplary sensor system.

Referencing FIG. 6, an embodiment of the invention allows for using a second probe 90 to measure the change in the oil's relative dielectric constant within the ultrasonic and sub-AM frequency bands. The second probe 90 may be an appropriately sized coaxial cable as shown in FIG. 6, which illustrates an exemplary sensor system 92. Probe 90 may include a coaxial circuit such as an elongated conductor portion 94 configured to be inserted within a sump of an internal combustion engine, for example, so that the distal end 96 may be immersed in oil that is contained within the sump. The portion 94 may be fabricated from a standard coaxial cable 98 with the distal end 96 exposed so it may be inserted within oil in the sump. Sensor system 92 may include an oscillator 100 for generating and controlling a frequency within the sub-AM band. A capacitance meter or detector 102, or other known device for measuring capacitance, may be provided for measuring the capacitance associated with probe 90. Probe 90 may measure the capacitance of the oil under investigation within the ultrasonic and sub-AM frequency bands. The difference between the baseline capacitance and the capacitance of the oil under investigation is indicative of the change in the oil's relative permittivity measured within the ultrasonic and sub-AM frequency band. Processor 76 may be configured to receive signals from detectors 72, 102 and calculate the percent of water and/or soot in the oil under investigation in accordance with the equations described above. It will be recognized that database 80 and display device 78, shown in FIG. 3, may be used with the sensor system 92.

Figure 7:
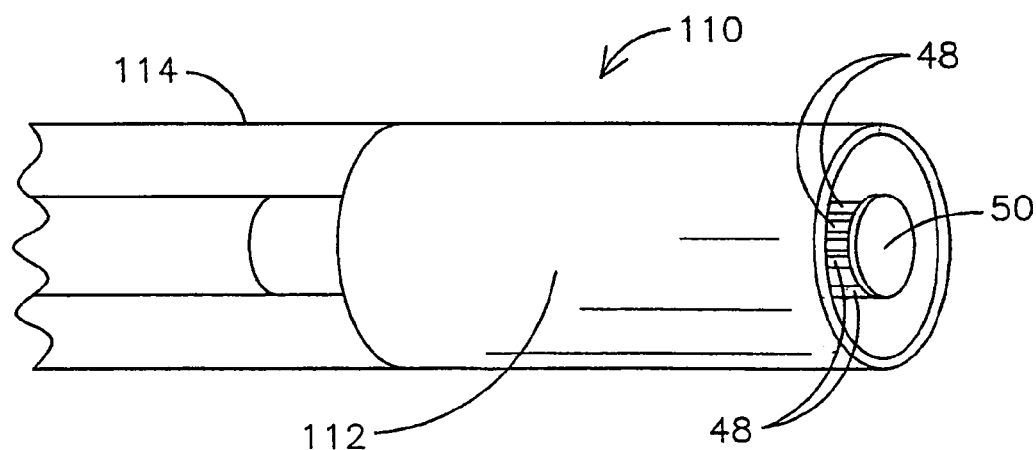
FIG. 7 is a partial perspective view of a probe for measuring a change in the relative permittivity of oil at microwave and sub-AM band frequencies.

Alternate embodiments allow for a single probe configuration 110, shown in FIG. 7, to be used for measuring changes in the relative dielectric constant of oil measured within the microwave and sub-AM band frequency ranges. Probe 110 may be configured with an embodiment of probe portion 38, shown best in FIG. 3, functioning as an inner conductor and encapsulated within an outer conductor 112. Probe 110 may be coupled with a coaxial cable 114, which may be operatively connected with a single oscillator, such as oscillator 60 or 100 for example, for generating microwave and sub-AM band frequencies. These frequencies may be controlled with known devices such as an appropriately configured varactor diode 66, which is shown as part of the oscillator 60 in FIG. 6. In an embodiment of probe 110, the outer conductor 112 may be about 0.28 inches in diameter, the inner conductor may be about 0.14 inches in diameter and probe 110 may be about 1.0 inch in length. This embodiment allows for the outer conductor 112 to operate within the ultrasonic and sub-AM frequency bands and inner conductor (probe 38) to operate within the microwave frequencies. A detector, such as detector 72 for example, may detect respective null level voltages along coaxial cable 32 associated with standing waves generated at microwave frequencies. The respective null level voltages may be used to calculate the changes in the relative dielectric constant of oil at microwave frequencies in accordance with aspects of the invention described above. Similarly, a capacitance detector, such as detector 102, may measure the capacitance associated with probe 110.

It will be appreciated that probe 110 may be used with embodiments of the invention shown in FIG. 6. In this respect, probe 110 may replace probe portion 38 and a capacitance detector may be incorporated as part of a sensor system. Other configurations and dimensions of probe 110 will be recognized by those skilled in the art as a function of the medium under investigation, frequencies being used, the medium's dielectric constant and/or the matter being detected within a medium.

It will be understood by those skilled in the art that exemplary embodiments of the present invention may be embodied in the form of computer code and/or computer-implemented processes and apparatus for practicing those processes. While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method of detecting soot and water content in diesel engine oil having a dielectric constant, the method comprising:
   measuring a change in the dielectric constant in a first frequency band;
   measuring a change in the dielectric constant in a second frequency band;
   using the measured changes in the dielectric constant in the first frequency band and the second frequency band to calculate the water content in the oil;
   using the measured changes in the dielectric constant in the first frequency band and the second frequency band to calculate the soot content in the oil; and
   using an imaginary part of the dielectric constant to calculate the soot content in the oil by determining the ratio of the difference between an oscillator tuning voltage generating a first standing wave passing through a portion of the oil having a first soot content and an oscillator tuning voltage generating a second standing wave passing through a portion of the oil having a second soot content over a null voltage level measured for the oil having the second soot content.

2. The method of claim 1 wherein the first frequency band is approximately within a sub-AM band of frequencies.

3. The method of claim 1 wherein the second frequency band is approximately within a microwave band of frequencies.

4. The method of claim 1 wherein the frequency in the first band is approximately 100 kilohertz.

5. The method of claim 1 wherein the frequency in the second band is approximately 10 gigahertz.

6. The method of claim 1 further comprising:
   transmitting data indicative of at least one of the soot content and the water content to a display device within a vehicle.

7. An apparatus for estimating a percentage of soot content or a percentage of water content in a medium having a dielectric constant, the apparatus comprising:
   means for measuring a change in the dielectric constant at a first frequency;
   means for measuring a change in the dielectric constant at a second frequency;

a processor configured to calculate at least one of a percentage of soot content and a percentage of water content as a function of the measured changes in the dielectric constant at the first and second frequencies;

the means for measuring a change in the dielectric constant at a second frequency comprising:

a variable frequency source for generating the second frequency band within a microwave frequency band;

a probe operatively coupled with the variable frequency source wherein at least a portion of the probe is immersed within the oil so that a standing wave is produced in response to each microwave frequency;

a detector for detecting a null voltage associated with each standing wave; and wherein the processor is configured to measure the change in the dielectric constant at the second frequency in response to the measured null voltage.

8. The apparatus of claim 7 further comprising:

a variable frequency oscillator for generating the first and second frequencies.

9. The apparatus of claim 7 wherein the first frequency is within approximately the sub-AM band of frequencies and the second frequency is within approximately the microwave frequency band.

10. The apparatus of claim 7, the means for measuring a change in the dielectric constant at a first frequency comprising:

a variable frequency source for generating the first frequency band within at least one of the ultrasonic and sub-AM frequency bands;

a probe operatively coupled with the variable frequency source wherein at least a portion of the probe is immersed within the oil so that a waveform of the first frequency passes within a portion of the oil; and a capacitance detector for measuring a capacitance associated with the waveform; and wherein the processor is configured to measure the change in the dielectric constant at the first frequency in response to the measured capacitance.

11. The apparatus of claim 7 further comprising:

means for controlling the microwave frequencies so that each null point of the standing wave for each frequency is placed at a detection point associated with the probe.

12. An apparatus for determining a concentration of soot and/or a concentration of water in diesel oil, the apparatus comprising:

at least one variable frequency source for generating one or more signals having different frequencies in a first frequency band and one or more signals having different frequencies in a second frequency band;

at least one probe operatively coupled with the at least one variable frequency source wherein at least a portion of the probe is immersed within the oil so that a respective waveform associated with the first frequency band and the second frequency band passes within a portion of the oil;

means for measuring a capacitance of the oil in response to the respective waveform associated with the first frequency passing through a portion of the oil;

a detector for detecting a null voltage level of respective waveforms associated with signals in the second frequency band; and a processor configured to measure a first change in a dielectric constant of the diesel oil in response to the measured capacitance and a second change in the dielectric constant in response to changes in voltage standing waveforms associated with signals in the second frequency band and calculate at least one of a concentration of soot and a concentration of water where each of the calculations is a function of the measured changes in the dielectric constant.

13. The apparatus of claim 12, the at least one probe comprising:

an inner conductor configured to operate with microwave frequencies; and an outer conductor configured to operate with at least one of an ultrasonic frequency band and a sub-AM frequency band.

* * * * *